United States Patent [19]
Harless

[11] Patent Number: 5,883,083
[45] Date of Patent: Mar. 16, 1999

[54] DIETARY SUPPLEMENT FOR ALLEVIATING BEHAVIORAL PROBLEMS IN CANINES AND REDUCING SEIZURES IN CANINES AND FELINES

[75] Inventor: Stanely James Harless, Omaha, Nebr.

[73] Assignee: Harlmen, Inc., Omaha, Nebr.

[21] Appl. No.: 871,400

[22] Filed: Jun. 9, 1997

[51] Int. Cl.⁶ ........................ A61K 31/205; A61K 31/685
[52] U.S. Cl. .............................. 514/78; 514/553; 514/556
[58] Field of Search ..................................... 514/562, 553, 514/556, 78

[56] References Cited

U.S. PATENT DOCUMENTS 5,308,832  5/1994  Garleb et al. ................................. 514/2
5,444,054  8/1995  Garleb et al. ............................... 514/54

OTHER PUBLICATIONS

Chemical Abstracts vol. 96: 211525u (Yoshida et al.) 1982.
Chemical Abstracts vol. 97: 196952g (Erber S. Dobler et al.) 1982.
Chemical Abstracts vol. 107: 90356a (Yoshida et al.) 1987.

*Primary Examiner*—Leonard Schenkman
*Attorney, Agent, or Firm*—Larson & Taylor

[57] ABSTRACT

A dietary supplement for canines and felines includes taurine in a liquid lecithin base. The dietary supplement has proven effective in reducing epileptic seizures in canines and in reducing behavioral problems, such as aggression, in canines. In addition, the dietary supplement is more easily digestible than conventional tablet forms of taurine and is more effectively administered to felines for treatment of cardiomyopathy.

15 Claims, No Drawings

DIETARY SUPPLEMENT FOR ALLEVIATING BEHAVIORAL PROBLEMS IN CANINES AND REDUCING SEIZURES IN CANINES AND FELINES

FIELD OF THE INVENTION

The present invention is directed to a dietary supplement for treatment of behavioral problems in canines and seizures in canines and felines and, more particularly, to a dietary supplement which includes taurine in a liquid lecithin base.

BACKGROUND OF THE INVENTION

Taurine is considered to be a metabolic factor involved in the conjugation and excretion of bile acids. Taurine is also a free amino acid present in most cells of the body including the adrenal glands, blood, cardiac muscle and brain. Taurine is a major constituent of the free amino acid pool in mammalian neural tissue, where it functions as a neurotransmitter or neuromodulator in the central nervous system. Taurine deficiency in the feline diet has been shown to be associated with the incidence of dilated cardiomyopathy, a condition in which the heart enlarges and becomes globular from the dilatation of the ventricles and the atria. Supplementing the diet of cats with taurine has proven effective in reducing the incidence of cardiomyopathy and as an anticonvulsant.

However, a major problem with taurine is the difficulty in administering it to animals. Taurine is an amino acid which is very bitter and only slightly soluble in water (one part of taurine to sixteen parts of water). Thus, taurine is typically administered in tablet form, which may not be digested in the short digestive tract of a cat (or a dog), thereby eliminating its usefulness.

Canines are known to suffer from seizures which are typically associated with epilepsy. Canines may also exhibit behavioral problems such as aggressiveness toward people and/or other animals or anxiety, such as when the animal is left alone by its owner, which may cause the animal to become destructive in the home. No nutritional supplement that is effective in eliminating these problems is available in the marketplace.

Accordingly, the need exists to provide an effective dietary supplement which alleviates behavioral problems in canines and reduces the occurrence of seizures in canines and felines.

SUMMARY OF THE INVENTION

Thus, it is a purpose of the present invention to overcome the disadvantages of the prior art and thereby provide a dietary supplement containing taurine which is palatable and easily digestible by both canines and felines.

In accordance with a preferred embodiment of the invention, the dietary supplement includes taurine in a lecithin base. Preferably, the lecithin base is a soy lecithin and is in liquid form. The dietary supplement is in the form of an emulsion which is formulated using an emulsifying agent such as carboxypolymethylene, cellulose, polysaccharides and acrylic copolymers. The dietary supplement also includes a preservative such as methylparaben and/or propylparaben. Additional preservatives or antioxidants, such as butylated hydroxyanisol ("BHA"), butylated hydroxytoluene ("BHT"), vitamin E, sodium benzoate, calcium propionate, potassium sorbate and sorbic acid, may also be utilized.

In a preferred embodiment of the invention, the dietary supplement includes the following compounds in percentage by weight: water 60–90%, methylparabens 0.1–0.2%, propylparabens 0.05–0.15%, emulsifying agent 0.1–1.0%, lecithin 1.0–6.0%, triethanolamide 0.01–2.0%, taurine 1.0–7.2%, sodium hydroxide 0.01–0.05%, citric acid 0.01–0.50%, water and flavor 0.37–0.70.

Because the dietary supplement is in a liquid form, it is easily digested by felines and canines. Administering the dietary supplement is also easier and provides a more effective means of administering taurine to canines to alleviate behavioral problems and the occurrence of epileptic seizures, and to felines to reduce the incidence of seizures.

It is, therefore, an object of the invention to provide a dietary supplement containing taurine which is easily digestible by canines and felines.

It is another object of the invention to provide a method of administering a dietary supplement to canines in an amount effective to alleviate epileptic seizures and behavioral problems such as aggression.

These and other objects of the present invention will become apparent from the detailed description to follow.

DESCRIPTION OF THE PREFERRED EMBODIMENTS

The dietary supplement of the present invention includes taurine in a lecithin base. Lecithin can be extracted from several sources including egg yolks and soybeans. Thus, lecithin is comprised of many different types and mixtures of phospholipids and glycolipids depending upon the source. The preferred lecithin is soybean lecithin, since it contains the exact same phospholipids found in the cell membrane (plasma membrane) of mammals. These phospholipids are phosphatidylcholine, phosphatidylethanolamine, phosphatidylinositol, and phosphatidylserine, which form the major phospholipids of the plasma membrane of the cell.

Lecithin provides three functions after ingestion. First, lecithin acts as an emulsifying agent to promote the rapid breakdown of food particles so digestive enzymes can more readily break down the substrates. This promotes digestion and absorption, which enhances the utilization of the fat soluble and water soluble vitamins.

Second, loading the diet with lecithin, i.e., a phospholipid rich supplement, promotes cellular repair and maintenance. In addition, lipid soluble chemicals move freely across the blood brain barrier. This is important because unless this barrier is voided by pathological changes or trauma, non-lipid soluble chemicals, other than water, do not enter the brain. Phospholipids can carry both water soluble and fat soluble chemicals across this barrier, since phospholipids are amphiphatic, having both hydrophilic and hydrophobic properties.

Third, lecithin contains diphosphatidylcholine, which is comprised of two molecules of choline and one molecule of glycerol. The body must have choline for the synthesis of acetylcholine, the major neurotransmitter in the central and peripheral nervous system. Supplementation with diphosphatidylcholine conserves the choline because it is absorbed as a phospholipid. Since the brain and peripheral nervous system is so dependent upon the neurotransmitter acetylcholine, supplementing the canine and feline diets with a lecithin containing large amounts of diphosphatidylcholine is an efficient method of choline loading, i.e. of supplementing choline in the body in a form that is not degraded by bacteria in the intestine, and can be absorbed by the cells.

Preferably, the lecithin base is enzyme modified to enhance water dispersibility and is also in the form of a liquid for ease in administering the dietary supplement. Thus, the dietary supplement further includes water which has been purified and an emulsifying agent. The emulsifying agent is generally a carboxypolymethylene or other hot and cold dispersible polymer such as cellulose, polysaccharide or an acrylic copolymer. A preferred carboxypolymethylene is Carbomer 934 which is available from various companies, including B F Goodrich.

Free molecules of taurine can be cross-linked to each other with the emulsifying agent which, in turn, adds stability to the emulsion. The added stability of the emulsion stabilizes the liposome microspheres. The emulsifying agent also tends to (1) micellize the liposomes to enhance emulsion stability and (2) coat the taurine molecules to reduce the bitter taste.

The dietary supplement of the invention also includes a stabilizer. The stabilizer may be any amine or alkalizer that is compatible with carboxylic acid systems. One suitable stabilizer is triethanolamide.

Preferred preservatives used in the dietary supplement are methylparaben and/or propylparaben. The dietary supplement may also contain other preservatives or antioxidants such as BHT, BHA, vitamin E, sodium benzoate, calcium propionate, potassium sorbate and sorbic acid. The preservative combination may be adjusted to achieve the proper hydrophilic and hydrophobic solubilities, i.e., since the dietary supplement is an emulsion containing both water and lecithin, an amphoteric compound, the preservatives must be compatible with both systems. Suitable acids and bases, such as citric acid and sodium hydroxide are utilized for adjustment of the pH in the range of 4.0 to 4.5. In addition, flavor and/or additional water may be added to the dietary supplement to improve palatability.

Although proper dosage of the dietary supplement is dependent upon the size of the animal and severity of the symptoms, the dosage of the liquid dietary supplement for canines will typically range between a total of 6 and 24 milliliters (ml) per day. The dietary supplement is preferably administered in divided daily dosages, as described in the examples below, although it may be administered more or less frequently. On average, the daily dosage for canines is 2 ml (approximately 150 milligrams (mg) of taurine) per 10 pounds of the animal's body weight. The daily dosage for cats is typically 4 ml per day.

In a preferred embodiment of the invention, the dietary supplement comprises the following compounds shown in weight percentages:

| Compound | % by Weight |
| --- | --- |
| Water | 60–90 |
| Methylparabens | 0.1–0.2 |
| Propylparabens | 0.05–0.15 |
| Emulsifying Agent | 0.1–1.0 |
| Lecithin | 1.0–6.0 |
| Triethanolamide | 0.01–2.0 |
| Taurine | 1.0–7.2 |
| Sodium Hydroxide | 0.01–0.05 |
| Citric acid | 0.01–0.50 |
| Flavor/additional water | 0.37–0.70 |

In a most preferred embodiment of the invention, the dietary supplement comprises the following:

| Compound | % by Weight |
| --- | --- |
| Water | 88.56 |
| Methylparabens | 0.18 |
| Propylparabens | 0.1 |
| Emulsifying Agent | 0.3 |
| Lecithin | 4.0 |
| Triethanolamide | 0.3 |
| Taurine | 6.65 |
| Sodium Hydroxide | 0.01–0.05 |
| Citric acid | 0.01–0.1 |
| Flavor/additional water | 0.16–0.29 |

Although the invention has been described in considerable detail with respect to preferred embodiments thereof, variations and modifications will be apparent to those skilled in the art without departing from the spirit and scope of the invention as set forth in the claims.

EXAMPLE 1

The dietary supplement was administered to a eight dogs, between 3 and 11 years of age, each having suffered from idiopathic epilepsy for varying periods of time between 5 and 64 months. The seizures were controlled, i.e., eliminated or reduced to less than two per year, by administering 3–12 ml of the dietary supplement twice daily.

EXAMPLE 2

The dietary supplement was administered to three male dogs, between 7 and 11 years of age, each having suffered from Petit or Grand mal seizures for periods of time between 11 and 42 months. The seizures were controlled by administering 4 ml of the dietary supplement twice daily.

EXAMPLE 3

The dietary supplement was administered to three male dogs and one female dog, between 1 and 6 years of age, each exhibiting aggressive behavior toward other dogs, cats and/or people. Aggression was reduced, i.e., dogs became more tolerant toward other animals/people by administering 4–12 ml of the dietary supplement twice daily.

EXAMPLE 4

The dietary supplement was administered to an eleven year old female dog. The dog had suffered from anxiety and pre-seizure behavior for 16 months. The anxiety was controlled by administering 3 ml of the dietary supplement twice daily.

EXAMPLE 5

The dietary supplement was administered to a ten year old cat. The cat had suffered from cardiomyopathy for 48 months. Progression of the condition was stopped by administering 4 ml of the dietary supplement once a day.

I claim:

1. A dietary supplement for canines and felines comprising 1.0–7.2% by weight taurine and 1.0–6.0% by weight soy lecithin.

2. The dietary supplement according to claim 1 further comprising an emulsifying agent.

3. The dietary supplement according to claim 2 wherein said emulsifying agent is selected from the group consisting of carboxypolymethylene, cellulose, polysaccharides and acrylic copolymers.

4. The dietary supplement according to claim 2 further comprising a preservative.

5. The dietary supplement according to claim 4 wherein said preservative is selected from the group consisting of methylparaben and propylparaben.

6. The dietary supplement according to claim 5 further comprising preservatives or antioxidants selected from the group consisting of BHT, BHA, vitamin E, sodium benzoate, calcium propionate, potassium sorbate and sorbic acid.

7. The dietary supplement according to claim 1 comprising the following compounds in percentage by weight: water 60–90%, methylparabens 0.1–0.2%, propylparabens 0.05–0.15%, emulsifying agent 0.1–1.0%, soy lecithin 1.0–6.0%, triethanolamide 0.01–2.0%, taurine 1.0–7.2%, sodium hydroxide 0.01–0.05%, and citric acid 0.01–0.50%.

8. A method of attenuating behavioral problems in canines comprising administering to a canine an effective amount of a dietary supplement comprising 1.0–7.2% by weight taurine and 1.0–6.0% by weight soy lecithin.

9. The method according to claim 8 wherein said dietary supplement further comprises an emulsifying agent selected from the group consisting of carboxypolymethylene, cellulose, polysaccharides and acrylic copolymers.

10. The method according to claim 9 wherein said dietary supplement further comprises a preservative is selected from the group consisting of methylparaben and propylparaben.

11. A method of alleviating seizures in canines comprising administering to a canine an effective amount of a dietary supplement comprising 1–7.2% taurine and 1–6% by weight soy lecithin.

12. The method according to claim 11 wherein said dietary supplement further comprises an emulsifying agent selected from the group consisting of carboxypolymethylene, cellulose, polysaccharides and acrylic copolymers.

13. The method according to claim 12 wherein said dietary supplement further comprises a preservative is selected from the group consisting of methylparaben and propylparaben.

14. The method of alleviating behavioral problems in canines comprising administering to a canine an effective amount of a dietary supplement comprising the following compounds in percentage by weight: water 60–90%, methylparabens 0.1–0.2%, propylparabens 0.05–0.15%, emulsifying agent 0.1–1.0%, soy lecithin 1.0–6.0%, triethanolamide 0.01–2.0%, taurine 1.0–7.2%, sodium hydroxide 0.01–0.05%, and citric acid 0.01–0.50%.

15. The method of alleviating seizures in canines comprising administering to a canine an effective amount of a dietary supplement comprising the following compounds in percentage by weight: water 60–90%, methylparabens 0.1–0.2%, propylparabens 0.05–0.15%, emulsifying agent 0.1–1.0%, soy lecithin 1.0–6.0%, triethanolamide 0.01–2.0%, taurine 1.0–7.2%, sodium hydroxide 0.01–0.05%, and citric acid 0.01–0.50%.

* * * * *